US010588903B2

(12) United States Patent
Hung et al.

(10) Patent No.: US 10,588,903 B2
(45) Date of Patent: Mar. 17, 2020

(54) METHODS AND COMPOSITIONS FOR ENHANCING IMMUNE RESPONSE TO VACCINATION

(71) Applicants: EMV Enhance (HK) Limited, Central (HK); VERSITECH LIMITED, Telegraph Bay (HK)

(72) Inventors: Fan Ngai Hung, Mid-Level (HK); Jinxia Zhang, Tai Po (HK); Kai Wang Kelvin To, Pokfulam (HK); Johnson Yiu-Nam Lau, Houston, TX (US); Kwok Yung Yuen, Pokfulam (HK)

(73) Assignees: EMV ENHANCE (HK) LIMITED, Hong Kong (HK); VERSITECH LIMITED, Hong Kong (HK)

( * ) Notice: Subject to any disclaimer, the term of this patent is extended or adjusted under 35 U.S.C. 154(b) by 0 days.

(21) Appl. No.: 15/745,411

(22) PCT Filed: Jul. 15, 2016

(86) PCT No.: PCT/US2016/042561
§ 371 (c)(1),
(2) Date: Jan. 16, 2018

(87) PCT Pub. No.: WO2017/015136
PCT Pub. Date: Jan. 26, 2017

(65) Prior Publication Data
US 2018/0207149 A1    Jul. 26, 2018

Related U.S. Application Data

(60) Provisional application No. 62/194,136, filed on Jul. 17, 2015.

(51) Int. Cl.
| A61K 31/4745 | (2006.01) |
| A61K 45/06 | (2006.01) |
| A61K 39/12 | (2006.01) |
| A61K 39/39 | (2006.01) |
| C07K 16/10 | (2006.01) |
| A61K 9/00 | (2006.01) |
| A61K 39/145 | (2006.01) |
| A61P 31/16 | (2006.01) |
| A61K 39/00 | (2006.01) |

(52) U.S. Cl.
CPC ........ A61K 31/4745 (2013.01); A61K 9/0014 (2013.01); A61K 39/12 (2013.01); A61K 39/145 (2013.01); A61K 39/39 (2013.01); A61K 45/06 (2013.01); A61P 31/16 (2018.01); C07K 16/1018 (2013.01); A61K 2039/54 (2013.01); A61K 2039/545 (2013.01); A61K 2039/55511 (2013.01); A61K 2039/55566 (2013.01); A61K 2039/575 (2013.01); C07K 2317/34 (2013.01); C07K 2317/76 (2013.01); C12N 2760/16134 (2013.01); C12N 2760/16234 (2013.01)

(58) Field of Classification Search
CPC .............. A61K 31/4745; A61K 39/145; A61K 9/0014; A61K 39/39; A61K 39/12; A61K 45/06; A61K 2039/55566; A61K 2039/575; A61K 2039/55511; A61K 2039/545; A61K 2039/54; A61K 2300/00; A61K 39/00; A61K 48/0075; A61K 31/713; A61K 2039/5252; A61P 31/16; C07K 16/1018; C07K 2317/76; C07K 2317/34; C07K 14/005; C12N 2760/16234; C12N 2760/16134; C12N 7/00; C12N 15/86; C12N 2760/16034; C07D 519/00
See application file for complete search history.

(56) References Cited

U.S. PATENT DOCUMENTS

2009/0060928 A1    3/2009    Bystryn

FOREIGN PATENT DOCUMENTS

| WO | 2005018574 | 3/2005 |
| WO | 2014145290 | 9/2014 |

OTHER PUBLICATIONS

Vasilakos JP, Tomai MA. The use of Toll-like receptor 7/8 agonists as vaccine adjuvants. Expert Rev Vaccines. Jul. 2013;12(7):809-19.*
Hung IF, Zhang AJ, To KK, Chan JF, Li C, Zhu HS, Li P, Li C, Chan TC, Cheng VC, Chan KH, Yuen KY. Immunogenicity of intradermal trivalent influenza vaccine with topical imiquimod: a double blind randomized controlled trial. Clin Infect Dis. Nov. 1, 2014; 59(9):1246-55. doi: 10.1093/cid/ciu582. Epub Jul. 21, 2014.*
Somagoni J, Boakye CH, Godugu C, Patel AR, Mendonca Faria HA, Zucolotto V, Singh M. Nanomiemgel—a novel drug delivery system for topical application—in vitro and in vivo evaluation. PLoS One. Dec. 29, 2014;9(12):e115952.*
Gunn D. Varicella-Zoster Vaccine and Herpes Simplex Virus: Is There Cross Immunity? Proc of UCLA Healthcare. vol. 20, 2016.*
Wong SS, Webby RJ. Traditional and new influenza vaccines. Clin Microbiol Rev. Jul. 2013;26(3):476-92.*

(Continued)

*Primary Examiner* — Rachel B Gill
(74) *Attorney, Agent, or Firm* — Fish IP Law, LLP

(57) ABSTRACT

Compositions and methods are described in which the topical application of a toll-like receptor 7 agonist or a toll-like receptor 9 agonist at or near a subdermal vaccination site provides an enhanced response to the vaccination. The enhanced response can be an elevated antibody titer relative to an untreated but vaccinated subject, and/or development of cross-species immunity to species not present in the vaccinating composition.

11 Claims, No Drawings

(56) References Cited

OTHER PUBLICATIONS

Szeimies RM, Bichel J, Ortonne JP, Stockfleth E, Lee J, Meng TC. A phase II dose-ranging study of topical resiquimod to treat actinic keratosis. Br J Dermatol. Jul. 2008;159(1):205-10. Epub Jul. 1, 2008.*
Dowling DJ. Recent Advances in the Discovery and Delivery of TLR7/8 Agonists as Vaccine Adjuvants. ImmunoHorizons Jul. 1, 2018, 2(6) 185-197.*
Petrovsky N. Comparative Safety of Vaccine Adjuvants: A Summary of Current Evidence and Future Needs. Drug Saf. Nov. 2015;38 (11):1059-74.*
Engel AL, Holt GE, Lu H. The pharmacokinetics of Toll-like receptor agonists and the impact on the immune system. Expert Rev Clin Pharmacol. Mar. 2011;4(2):275-89.*
Zheng M, Liu F, Shen Y, Wang S, Xu W, Fang F, Sun B, Xie Z, Chen Z. Cross-protection against influenza virus infection by intranasal administration of nucleoprotein-based vaccine with compound 48/80 adjuvant. Hum Vaccin Immunother. 2015;11(2):397-406.*
Zhang AJ, Li C, To KK, Zhu HS, Lee AC, Li CG, Chan JF, et. al. Toll-like receptor 7 agonist imiquimod in combination with influenza vaccine expedites and augments humoral immune responses against influenza A(H1N1)pdm09 virus infection in BALB/c mice. Clin Vaccine Immunol. Apr. 2014;21(4):570-9. Epub Feb. 12, 2014.*
Fehres CM, Bruijns SC, van Beelen AJ, Kalay H, Ambrosini M, Hooijberg E, Unger WW, et. al. Topical rather than intradermal application of the TLR7 ligand imiquimod leads to human dermal dendritic cell maturation and CD8+ T-cell cross-priming. Eur J Immunol. Aug. 2014;44(8):2415-24. Epub May 13, 2014.*
PCT Search Report and Written Opinion dated Oct. 25, 2016 for PCT/US2016/042561 entitled Methods and Compositions for Enhancing Immune Response to Vaccination filed on Jul. 15, 2016.
Hung, Ivan F.N. et al, "Immunogenicity of Intradermal Trivalent Influenza Vaccine With Topical Imiquimod: A Double Blind Randomized Controlled Trial" printed in Clinical Infectious Diseases (CID), Nov. 1, 2014, pp. 1247-1255.
Othoro, Caroline et al, "Enhanced Immunogenicity of Plasmodium falciparum Peptide Vaccines Using a Topical Adjuvant Containing a Potent Synthetic Toll-Like Receptor 7 Agonist, Imiquimod" printed in Infection and Immunity dated Feb. 2009, pp. 739-748.
Thomsen LL, Topley P, Daly MG, Brett SJ, Tite JP. Imiquimod and resiquimod in a mouse model: adjuvants for DNA vaccination by particle-mediated immunotherapeutic delivery. Vaccine. 2004;22:1799-809.
Zuber AK, Bråve A, Engström G, Zuber B, Ljungberg K, Fredriksson M, et al. Topical delivery of imiquimod to a mouse model as a novel adjuvant for human immunodeficiency virus (HIV) DNA. Vaccine. 2004;22:1791-8.
Kanekiyo M, Wei CJ, Yassine HM, McTamney PM, Boyington JC, Whittle Jr, et al. Self-assembling influenza nanoparticle vaccines elicit broadly neutralizing H1N1 antibodies. Nature 2013;499:102-6.
Montana M, Verhaeghe P, Ducros C, Terme T, Vanelle P, Rathelot P. Safety review: squalene and thimerosal in vaccines. Therapie 2010;65:533-41.
Black S, Della Cioppa G, Malfroot A, Nacci P, Nicolay U, Pellegrini M, et al. Safety of MF59-adjuvanted versus non-adjuvanted influenza vaccines in children and adolescents: an integrated analysis. Vaccine 2010;28:7331-6.
Toll-Like Receptor 7 Agonist Imiquimod in Combination with Influenza Vaccine Expedites and Augments Humoral Immune Responses against Influenza A(H1N1)pdm09 Virus Infection in BALB/c Mice by Anna J. X. Zhang et al., Apr. 2014 vol. 21 No. 4 Clinical and Vaccine Immunology p. 570-579.
Effect of Adjuvants on Responses to Skin Immunization by Microneedles Coated with Influenza Subunit Vaccine William C. Weldon et al, PLoS ONE | www.plosone.org; Jul. 2, 2012, vol. 7, Issue 7 (1-8 pages).
Interim estimates of 2014/15 vaccine effectiveness against influenza A(H3N2) from Canada's Sentinel Physician Surveillance Network, Jan. 2015 by D M Skowronski et al., www.eurosurveillance.org (1-18).

* cited by examiner

METHODS AND COMPOSITIONS FOR ENHANCING IMMUNE RESPONSE TO VACCINATION

This application claims the benefit of U.S. Provisional Patent Application No. 62/194,136 filed on Jul. 17, 2015. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is adjuvants for use with vaccine formulations, particularly influenza vaccine formulations.

BACKGROUND

The background description includes information that may be useful in understanding the present invention. It is not an admission that any of the information provided herein is prior art or relevant to the presently claimed invention, or that any publication specifically or implicitly referenced is prior art.

Influenza poses a heavy burden to our health service (1, 2), causing significant morbidity and mortality in older people, very young children and persons with chronic illness. Seasonal, zoonotic and pandemic influenza are constant global threats. The World Health Organization estimates that seasonal influenza causes 250,000-500,000 deaths worldwide each year. Most recently, the antigenically drifted A/Switzerland/9715293/2013 virus caused major outbreaks in various countries in Europe and North America (CDC Health Advisory regarding the potential for circulation of drifted influenza A (H3N2) viruses.(see emergency-.cdc.gov/HAN/han00374.asp); Skowronski D M, Drews S J, Fonseca K, Charest H, Chambers C, Sabaiduc S, et al. Interim estimates of 2014/5 vaccine effectiveness against influenza A (H3N2) from Canada's sentinel physician surveillance network. Euro Surveill 2015; 20. Pi: 21022). Virological surveillance of influenza A(H3N2) viruses collected in the United States from Oct. 1 through Nov. 22, 2014 showed that 52% of these isolates were antigenically drifted from the A/Texas/50/2012(H3N2) vaccine virus (4). All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Moreover avian influenza viruses such as the A(H5N1) and more recently A(H7N9), the spread of which from their regions of origin is facilitated by air travel, are often associated with a much higher mortality than traditional seasonal influenza. As such, the protective potential of immunizing formulations based on predictions of likely pathogenic strains made well in advance of actual outbreaks is necessarily limited.

One approach to addressing this problem is to increase the complexity of the vaccinating formulation. For example, co-circulation of Influenza B Yamagata and Victoria strains leading to seasonal outbreaks resulted in a call for the routine use of a quadrivalent influenza vaccine. Such an approach, however, further complicates production of seasonal influenza vaccines and does not address the fundamental issue of genetic drift from predicted strains and unanticipated introduction of new influenza strains.

Imiquimod, a synthetic toll-like receptor 7 (TLR7) agonist useful for the treatment of DNA virus infection, has been found to improve certain aspects of influenza vaccine immunogenicity in experimental animal models (Thomsen L L, Topley P, Daly M G, Brett S J, Tite J P. Imiquimod and resiquimod in a mouse model: adjuvants for DNA vaccination by particle-mediated immunotherapeutic delivery. Vaccine. 2004; 22:1799-809; Zuber A K, Bråve A, Engström G, Zuber B, Ljungberg K, Fredriksson M, et al. Topical delivery of imiquimod to a mouse model as a novel adjuvant for human immunodeficiency virus (HIV) DNA. Vaccine. 2004; 22:1791-8; Weldon W C, Zarnitsyn V G, Esser E S, Taherbhai M T, Koutsonanos D G, Vassilieva E V, et al. Effect of adjuvants on responses to skin immunization by microneedles coated with influenza subunit vaccine. PLoS One. 2012; 7:e41501; Zhang A J, Li C, To K K, Zhu H S, Lee A C, Li C G, et al. Toll-like receptor 7 agonist imiquimod in combination with influenza vaccine expedites and augments humoral immune responses against influenza A(H1N1) pdm09 virus infection in BALB/c mice. Clin Vaccine Immunol. 2014; 21:570-9). For example, treatment with topical imiquimod before intradermal trivalent influenza vaccine expedited, augmented and prolonged the immunogenicity against the immunizing influenza vaccine strains in elderly subjects with chronic illness (Hung I F, Zhang A J, To K K, Chan J F, Li C, Zhu H S, et al. Immunogenicity of intradermal trivalent influenza vaccine with topical imiquimod: a double blind randomized controlled trial. Clin Infect Dis 2014; 59:1246-55). Similar studies have noted a boost in immune response to vaccinating species as an effect of a topical TLR7 agonist, imiquimod in both human and animal models. The immunity induced was rapid and could sustain beyond the one-year period in immunosenescent elderly subjects. An imiquimod adjuvanted (i.e. mixed and injected with the vaccine formulation) vaccine has also been found to elicit higher level of IgG2a antibodies, HI titers and IFN-γ cellular response directed to immunizing species when compared to vaccine alone. Simultaneous subcutaneous administration of imiquimod as an adjuvant with DNA vaccine also enhanced the dendritic cell and Th1 lymphocyte response towards the injected antigens in mouse model (Thomsen L L, Topley P, Daly M G, Brett S J, Tite J P. Imiquimod and resiquimod in a mouse model: adjuvants for DNA vaccination by particle-mediated immunotherapeutic delivery. Vaccine. 2004; 22:1799-809; Zuber AK, Bråve A, Engström G, Zuber B, Ljungberg K, Fredriksson M, et al. Topical delivery of imiquimod to a mouse model as a novel adjuvant for human immunodeficiency virus (HIV) DNA. Vaccine. 2004; 22:1791-8). Such an increased response to vaccinated species, however, does not address issues resulting from antigenic drift or introduction of new influenza virus strains that are not present in a vaccinating formulation to a population.

Other strategies have been studied to improve the immunogenicity and breadth of the influenza vaccine by targeting the relatively conserved hemagglutinin stem, the M2 and the nucleoprotein, or by changing the mode of delivery with viral vectors. More recently, the development of self-assembling synthetic nanoparticle vaccine was also found to improve the potency and breadth of influenza virus immunity (Kanekiyo M, Wei C J, Yassine H M, McTamney P M, Boyington J C, Whittle J R, et al. Self-assembling influenza nanoparticle vaccines elicit broadly neutralizing H1N1 antibodies. Nature 2013; 499:102-6). Nevertheless, such strategies are still confined to the stage of cell-line or animal studies. The use of adjuvants including the MF59 or AS03 has demonstrated an antigen sparing effect with improved immunogenicity. Unfortunately, ] frequent local adverse events limit its utility (Montana M, Verhaeghe P, Ducros C, Terme T, Vanelle P, Rathelot P. Safety review: squalene and thimerosal in vaccines. Therapie 2010; 65:533-41; Black S, Della Cioppa G, Malfroot A, Nacci P, Nicolay U, Pellegrini M, et al. Safety of MF59-adjuvanted versus non-adjuvanted influenza vaccines in children and adolescents: an integrated analysis. Vaccine 2010; 28:7331-6). In addition the dose sparing effect is less pronounced in individuals who have been primed earlier in their lives with antigenically related viruses or vaccines. Therefore, the application of topical imiquimod pretreatment before intradermal influenza vaccination is the most simple and readily available strategy to improve and broaden the influenza vaccine immunogenicity. It has also been noted that the combination of synthetic TLR4 and TLR7 ligands can act as an adjuvant when coinjected with recombinant influenza virus hemagglutinin, and can stimulate both Th1 and Th2-type immune responses in mice, thereby providing broad neutralizing antibodies against the antigenically drifted influenza viruses (18). It is not clear, however, how effective such approaches will be in widespread immunization efforts.

Thus, there is still a need for a simple, effective, and well tolerated compositions and methods that provide an enhanced immune response and/or broadened range of effective responses to vaccine formulations

SUMMARY OF THE INVENTION

The inventive subject matter provides compositions and methods that enhance an immune response of a treated subject to a vaccinating compositions. This is accomplished by applying a topical preparation that includes a toll-like receptor 7 agonist to the skin surrounding an area where a transdermal vaccination is applied. Enhanced immune responses include: (1) improved antibody titer relative to that produced by administration of the vaccine in the absence of application of the topical preparation, and (2) generation of an effective immune response to species not present in the vaccinating composition.

One embodiment of the inventive concept is a method of improving an immune response to vaccination by applying a topical formulation to a vaccination site at or immediately prior to vaccination, where the topical formulation comprising a toll-like receptor 7 agonist and/or a toll-like receptor 9 agonist. In such a method a vaccine (which includes a vaccinating species, such as trivalent influenza vaccine, multivalent influenza vaccine, and/or a coronavirus vaccine) is also applied at the vaccination site. A barrier can be applied to the treated area following application of the topical preparation and/or administration of the vaccine. In some embodiments the topical preparation is applied within 5 minutes of the administration of the vaccine. After a period of time (for example, 1 to 6 hours) following application of the vaccine the topical formulation is removed. The topical formulation is selected to provide a toll-like receptor 7 agonist and/or a toll-like receptor 9 agonist in a quantity sufficient to provide effective protection against a non-vaccinating species that is not present in the vaccine, and or to an improved antibody titer to the vaccinating species, relative to an antibody titer generated on vaccination without the topical formulation. In some embodiments the vaccinating species includes an influenza virus and/or a coronavirus. In some embodiments the non-vaccinating species includes a different influenza virus and/or a different coronavirus from that/those represented in the vaccinating species. In a preferred embodiment the toll-like receptor 7 agonist comprises imiquimod. In some embodiments the topical formulation is formulated to provide between about 2 mg and about 20 mg of the toll-like receptor agonist to the skin. In some embodiments the topical formulation is provided as a nano-emulsion of the toll-like receptor 7 agonist and/or a toll-like receptor 9 agonist. In still other embodiments the topical formulation is supplied as part of an application device.

Another embodiment of the inventive concept is the use of a toll-like receptor 7 agonist and/or a toll-like receptor 9 agonist in the preparation of a topical formulation that provides an enhanced response to a vaccine (for example, a trivalent influenza vaccine, multivalent influenza vaccine, and/or a coronavirus vaccine). The enhanced response includes development of a protective immune response to a species that is not present in a vaccine used to immunize a vaccinated subject treated with the topical formulation. Such a vaccine can include an influenza virus and/or a corona virus, in which case a protective immune response is elicited to a different influenza virus and/or coronavirus. In some embodiments such an enhanced immune response includes development of an improved antibody titer to a species present in the vaccine, relative to vaccination response achieved in a vaccinated subject that has not been treated with the topical formulation. In a preferred embodiment the toll-like receptor 7 agonist is imiquimod. In some embodiments the topical formulation is formulated to provide between 2 mg and 20 mg of the toll-like receptor 7 agonist and/or a toll-like receptor 9 agonist on application. In still other embodiments the topical formulation is provided as part of an appliance.

Another embodiment of the inventive concept is the use of a toll-like receptor 7 agonist and/or a toll-like receptor 9 agonist in the preparation of a kit that provides an enhanced response to a vaccine (for example, a trivalent influenza vaccine, multivalent influenza vaccine, and/or a coronavirus vaccine). The enhanced response includes development of a protective immune response to a species that is not present in a vaccine used to immunize a vaccinated subject treated with the topical formulation. Such a vaccine can include an influenza virus and/or a corona virus, in which case a protective immune response is elicited to a different influenza virus and/or coronavirus. In some embodiments such an enhanced immune response includes development of an improved antibody titer to a species present in the vaccine, relative to vaccination response achieved in a vaccinated subject that has not been treated with the topical formulation. In a preferred embodiment the toll-like receptor 7 agonist is imiquimod. In some embodiments the topical formulation is formulated to provide between 2 mg and 20 mg of the toll-like receptor 7 agonist and/or a toll-like receptor 9 agonist on application. In still other embodiments the topical formulation is provided as part of an appliance, for example an appliance that adheres to the skin. In some embodiment the kit can include a barrier, film and/or a microneedle device.

DETAILED DESCRIPTION

The following description includes information that may be useful in understanding the present invention. It is not an admission that any of the information provided herein is prior art or relevant to the presently claimed invention, or that any publication specifically or implicitly referenced is prior art.

The inventive subject matter provides compositions and methods in which a composition containing a toll-like receptor 7 agonist and/or a toll-like receptor 9 agonist is applied topically at or near a virus vaccine injection site, either at or immediately prior to the time of vaccination. The resulting immune response to the vaccination is enhanced in providing both a higher titer immune response to vaccinating viral species (relative to a response observed in the absence of the topically applied composition) and in providing an effective immune response to viral strains not found in the immunizing composition. Suitable viral species include influenza and/or coronavirus species. Various objects, features, aspects and advantages of the inventive subject matter will become more apparent from the following detailed description of various illustrative and preferred embodiments.

One should appreciate that the disclosed techniques provide many advantageous technical effects including improving the effectiveness and breadth of protection afforded by viral vaccination preparations without the need for reformulation of the vaccine.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The inventors have found that toll-like receptor 7 agonists (such as imiquimod) and/or a toll-like receptor 9 agonist can be applied topically (for example, as an ointment) to provide enhanced immune response to viral vaccine preparations. In a preferred embodiment, the vaccine preparation includes viral antigens corresponding to seasonal influenza species/strains (for example, monovalent, divalent, trivalent, and/or multivalent influenza vaccines) and/or coronaviruses. The enhanced immune response can be observed on application of the toll-like receptor 7 agonist and/or a toll-like receptor 9 agonist at the time of vaccination, immediately prior to or following vaccination. For example, a toll-like receptor 7 agonist and/or a toll-like receptor 9 agonist composition of the inventive concept can be applied to the surface of the skin at and/or around a vaccination injection site less than or equal to 1 hour, less than or equal to 30 minutes, less than or equal to 20 minutes, less than or equal to 10 minutes, less than or equal to 5 minutes, less than or equal to 2 minutes, or less than or equal to 1 minute prior to vaccination. Similarly, in other embodiments the toll-like receptor agonist composition can be applied 1 hour, less than or equal to 30 minutes, less than or equal to 20 minutes, less than or equal to 10 minutes, less than or equal to 5 minutes, less than or equal to 2 minutes, or less than or equal to 1 minute following vaccination. Following application and/or vaccination, the toll-like receptor 7 agonist and/or a toll-like receptor 9 agonist composition can be left in place on the skin surface for a period of time. For example, a toll-like receptor 7 agonist and/or a toll-like receptor 9 agonist composition can be left in place for at least 15 minutes, at least 30 minutes, at least one hour, at least 2 hours, at least 3 hours, at least 6 hours, at least 12 hours, at least 16 hours, or 24 hours or more following vaccination. In some embodiments the area of skin treated with the toll-like receptor 7 agonist and/or a toll-like receptor 9 agonist containing composition can be protected by a barrier, such as a barrier film or bandage, during this post-vaccination period.

Vaccination can be performed by any suitable method. Suitable methods include sub- or intra-dermal injection, intramuscular injection, and microneedle vaccination. Such microneedle vaccination can be carried out using a microneedle device or through the use of a microneedle patch. Similarly, immunization can be carried out transcutaneously using methods that disrupt the stratum corneum layer of the skin, including tape stripping and disruption using laser and/or ultrasound energy.

In embodiments of the inventive concept, a topical preparation that includes a toll-like receptor 7 agonist and/or a toll-like receptor 9 agonist can be applied to an area at or near that of the site of vaccination. In some embodiments of the inventive concept, such a topical preparation can be applied to an area of about 1 $cm^2$ that surrounds the site of vaccination. In other embodiments the area treated using the topical preparation can be about 4 $cm^2$, 9 $cm^2$, 16 $cm^2$, or more surrounding the site of vaccination. In embodiments of the inventive concept the area treated with the topical preparation at least partially overlaps the site of vaccination. In a preferred embodiment the site of vaccination can be approximately centered in the topically treated area.

Some embodiments of the inventive concept include an applicator or application device that can assist a healthcare provider with proper utilization of such a topical preparation. Such a device can be utilized following application of the topical preparation to the skin surface. In other embodiments such a device can be applied simultaneously with application of the topical preparation to the skin surface. In such embodiments the topical preparation can be included with and/or form part of the application device. Suitable application devices can include a barrier (such as a barrier film), which can prevent transfer of an applied topical preparation from the skin surface. Such a barrier film can be secured to a skin surface by any suitable means, for example an adhesive, elastic bandage, or pressure from a garment. Alternatively, in some embodiments the topical preparation can be formulated to provide adhesion of such a barrier film. For example, a component of the vehicle of the topical preparation can be selected to provide sufficient traction and/or adhesion to at least transiently fix a barrier film to a treated skin surface (for example, by providing a moist, tacky, and/or gelatinous surface texture). In some embodiments of the inventive concept such a kit can include a template or similar representation of an area over which the topical preparation is to be applied. Such a template can include an indication of the desired vaccination site, and in some embodiments can at least transiently adhere to the skin surface.

Another embodiment of the inventive concept is a kit for utilization of a topical preparation that includes a toll-like receptor 7 agonist and/or a toll-like receptor 9 agonist. Such a kit can be used to enhance a patient's response to vaccination. Such a kit can include a topical preparation that includes a toll-like receptor 7 agonist and/or a toll-like receptor 9 agonist in a pharmaceutically acceptable medium and an application device as described above. In some embodiments such a kit can include instructions for use. Such instructions can include directions for timing of the application of the topical preparation relative to the delivery of the vaccine to the patient, time that the topical preparation is to be kept in place on the treated skin surface, instructions for removal of the topical preparation from the skin surface, and/or instructions for aftercare of the vaccination and/or treated site.

Suitable toll-like receptor 7 agonists include imiquimod, CL075, CL097, CL264, CL307, Gardiquimod™, loxoribine, and R848. Suitable toll-like receptor 9 agonists include agatolimod, MGN1703, CPG 7909, PF-3512676, ISS 1018, IMO-2055, and CpG-28. A topically applicable composition containing such a toll-like receptor 7 agonist and/or a toll-like receptor 9 agonist can include a pharmaceutically acceptable vehicle, and can be formulated as a spray, lotion, ointment, gel, emulsion, micro-emulsion, nano-emulsion, or other suitable solution and/or suspension. Such topical formulations can be formulated to provide from about 0.1 mg, 1 mg, 2.5 mg, 5 mg, 7.5 mg, 10 mg, 12.5 mg, 15 mg, 20 mg or more of the toll-like receptor 7 agonist and/or a toll-like receptor 9 agonist to an individual on application of the formulation. Optionally, such a topical formulation can include an indicator, for example a dye, to provide a visible indication that an area of skin has been treated. In some embodiments, the toll-like receptor 7 and/or a toll-like receptor 9 agonist composition is provided as part of a patch that adheres to the skin surface, and which applies the toll-like receptor 7 agonist and/or a toll-like receptor 9 agonist to the skin while additionally providing a barrier film. Such a patch can be formulated to permit vaccination through the material of the patch following application. In some embodiments, the topical formulation includes a nano-emulsion of the toll-like receptor 7 agonist and/or a toll-like receptor 9 agonist, which can speed absorption of the toll-like receptor 7 agonist and/or a toll-like receptor 9 agonist relative to conventional suspensions, solutions, and/or emulsions. In other embodiments, the topical formulation is applied with microneedles (for example, a microneedle array or patch).

It should be appreciated that two distinct and different forms of enhanced vaccination response can be generated through the use of a topically applied toll-like receptor 7 agonist and/or toll-like receptor 9 agonist. In one form of enhanced vaccination response, a quantifiable immune response (for example, antibody titer) to an immunizing species or viral strain is enhanced (i.e. improved) in an individual or population receiving topical treatment at the vaccination site with a toll-like receptor 7 agonist and/or a toll-like receptor 9 agonist relative to an equivalently vaccinated control (e.g. receiving the same vaccination) that does not receive such topical treatment. For example, an individual or population receiving topical treatment with a toll-like receptor 7 agonist and/or a toll-like receptor 9 agonist at or near a vaccination site can have a 1.5 fold, 2 fold, 3 fold, 4 fold, 5 fold 6 fold 7 fold, 8 fold, 10 fold or higher GMT (geometric mean titer) for a vaccinating influenza species or strain than that observed from a control individual or population receiving the same vaccine by the same route of administration, but lacking the topical treatment.

Another form of enhanced vaccination response can be the induction of a functional immunity to viral species or strains that are not present in the vaccine formulation used to vaccinate an individual that receives topical treatment with a and/or a toll-like receptor 9 agonist agonist at or near the site of vaccination (i.e. cross protection). For example, an individual or population receiving topical treatment with a toll-like receptor 7 agonist and/or a toll-like receptor 9 agonist at or near a vaccination site can develop an effective immune response (for example, antibody titer) to an influenza species or strain that does not form part of the vaccinating mixture, whereas such a protective response to the non-vaccinating species or strain is not observed from a control individual or population receiving the same vaccine by the same route of administration, but lacking the topical treatment. In some embodiments both types of enhanced vaccination response are produced.

Methods

In a double-blind, randomized controlled trial, healthy volunteers aged 18-30 years in early 2014 received the 2013-14 northern hemisphere winter trivalent influenza vaccine (TIV). Eligible subjects were randomly allocated (1:1:1:1) into 4 groups: topical imiquimod ointment followed by intradermal TIV (IQ), topical aqueous-cream followed by intradermal TIV (ID), topical aqueous-cream followed by intramuscular TIV (IM), and topical imiquimod ointment followed by intradermal normal saline injection (NS). Volunteers and investigators were blinded to the type of topical treatment applied. Hemagglutination inhibition (HI) and neutralization antibody titers (NT) were measured. Primary outcome was day 7 seroconversion rate. Other outcomes included seroprotection rate and GMT-fold increase against the vaccine and non-vaccine strains (including the A/Switzerland/9715293/2013-like virus which emerged in late 2014) at day 7 and 21.

Study Design and Interventions

At the time of inclusion, demographic data of the participants were obtained. Simple randomization with no stratification was performed. Participants were randomly assigned into 4 groups, the experimental group (IQ) and three control groups (ID, IM and NS respectively). A square of 16 cm$^2$ was marked on the deltoid region of the right arm of all participants by the study nurse. In the IQ and NS groups, the study nurse would apply the content of one sachet of Aldara™ (5%, 12.5 mg of imiquimod in 250 mg cream) to the marked surface on the skin 5 minutes before vaccination. In the ID and IM groups, aqueous cream BP™ (AFT pharmaceuticals, New Zealand) with no effect was applied instead of the Aldara™ by the study nurse. Participants in the IQ and ID groups received a single dose of 0.1 mL intradermal influenza trivalent vaccine (15 µg of hemagglutinin [HA] per strain). In the IM group, participants received a single dose of 0.5 mL intramuscular influenza vaccine (15 µg of hemagglutinin per strain). In the NS group, participants received a single dose of 0.1 mL of normal saline as sham vaccine. The vaccine was injected in the center of the marked area after the cream was absorbed and skin disinfection by 70% alcoholic swab. The ointment (Aldara™ or aqueous cream BP) was removed by the participant by washing with tap water 6 hours after vaccination.

To maintain blinding, each participant was assigned to a serial number, and the randomization list linked each serial number with the 4 study groups, differed in the route of delivery and the type of pre-treatment ointment applied. Only the study nurse had knowledge of the type of topical treatment applied. Both participants and investigators remained blinded to the type of topical treatment applied until the completion of the study. The route of delivery was unblinded to the participants during vaccination.

Influenza Vaccine

Both the intradermal Intanza™15 (Sanofi-Pasteur, Lyon, France) and the intramuscular Vaxigrip™ (Sanofi-Pasteur, Lyon, France) influenza vaccines used were manufactured by Sanofi-Pasteur MSD™. Both vaccines were inactivated, non-adjuvanted vaccines formulated to contain 15 µg of HA of influenza A/California/07/2009 (H1N1)-like virus, influenza A/Victoria/361/2011 (H3N2)-like virus and influenza B/Massachusetts/2/2012-like virus (B/Yamagata lineage). The intradermal injection device, the BD Soluvia™ microinjection system consists of a prefilled trivalent influenza vaccine, with a single 1.5 mm needle penetrating perpendicularly to the skin. The BD Soluvia™ is currently the only prefilled intradermal device licensed for influenza vaccine.

Safety was evaluated by first asking the subjects to remain in the clinic premise for 30 minutes for post-immunization observation. An immediate adverse event checklist was filled before discharge, covering the period for severe anaphylactic reaction. In addition, a diary was given to the subjects to document symptoms of local and systemic adverse events presented within the first 7 days post-vaccination. Systemic symptoms included fever (body temperature≥37.5° C.), headache, malaise, myalgia, arthralgia and severe adverse events, and local symptoms included redness, swelling, induration, ecchymosis and pain were documented as solicited events. Redness, swelling, induration, and ecchymosis were graded based on size: grade 1<20 mm and grade 2>20 mm. Pain was graded accordingly: grade 1 was pain on touch and grade 2 was pain when arm was moved. The diaries were collected upon follow-up on day 21-post vaccination.

Immunogenicity Measurements

Blood was taken from participants at baseline, 7 and 21 days after vaccination for antibody assay. Serum antibody titer was measured using a hemagglutination-inhibition (HI) assay for the vaccine strains, and by both HI and neutralization antibody (NT) assays for the non-vaccine strains, according to standard methods. The Committee for Proprietary Medicinal Products (CPMP) guidelines of the European Medicines Evaluation Agency was adopted for immunogenicity measurements of the HI assay. A satisfactory (i.e. effective) antibody response in adult subjects, aged between 18 and 60 is based on at least one of the following indicated requirements: 1) >70% achieving a HI titer of ≥40 (seroprotection rate) or 2) a geometric mean titer (GMT) fold increase>2.5-fold or 3) >40% achieving a 4-fold rise in antibody titer (seroconversion rate). For the NT assay, the GMT of the four non-vaccine strains was compared among the 4 groups.

A primary outcome measure is the seroconversion rate by HI assay on day 7. Secondary outcome measures included GMT, GMT fold increases and the seroprotection rate by HI assay and the GMT by NT assay from day 7 and 21 post vaccination. The seroconversion rate by HI assay from day 7 and 21 and adverse events post-vaccination were also compared among the 4 groups.

In addition, in order to assess the cross-protection effect to the four non-vaccine influenza strains: A/HK/485197/14 (H3N2 Switzerland lineage), A/HK/408027/09 (prepandemic seasonal H1N1), A/WSN/33 (H1N1), B/HK/418078/11 (Victoria lineage) by imiquimod pretreatment before TIV vaccination, the seroprotection, seroconversion and GMT fold increase by HI and NT assay against these virus strains were measured on day 7 and 21 after vaccination.

Hemagglutination-inhibition Assay

Paired serum samples (pre- and post-vaccination) were tested for hemagglutination-inhibiting (HI) antibody using reference antigens including the three vaccine strains: A/California/07/2009 (H1N1)-like virus, influenza A/Victoria/361/2011 (H3N2)-like virus and influenza B/Massachusetts/2/2012-like virus (B/Yamagata lineage), and the four non-vaccine strains as stated above. HI antibody assays were performed by standard microtiter techniques after removal of non-specific inhibitors in serum by pre-absorption with turkey erythrocytes for A(H1N1) antibody testing or guinea pig erythrocytes for A(H3N2) & B antibody testing, and followed by receptor destroying enzyme (RDE) (1:3) after incubation overnight at 37° C. before heat-inactivation at 56° C. for 30 minutes. All serum samples from each subject were tested in parallel for each of the test antigens. Serial two-fold dilutions of RDE-treated serum from 1:10 were titrated against 4 hemagglutinin units of reference antigens using 0.5% turkey or 0.75% guinea pig erythrocytes.

Neutralization Antibody Assay

The Neutralizing Antibody assay (NT) was performed in 96-well microwell plates seeded with Madin Darby canine kidney cells. Two fold serial dilutions of paired serum (pre- and post-vaccination) were tested in duplicate by inoculation with 100 TCID$_{50}$ of A/HK/485197/14 (H3N2 Switzerland lineage), A/HK/408027/09 (pre-pandemic seasonal H1N1), A/WSN/33 (H1N1), B/HK/418078/11 (Victoria lineage) viruses. A corresponding set of cell controls with sera but without virus inoculation was used as controls. The cells were scored for inhibition of the cytopathic effect (CPE) at 72 hours after inoculation. The titer of a neutralization antibody is defined as the maximum dilution of serum at which the percentage of CPE is less than or equal to 50%.

Statistical Analysis

The sample size of this study was determined based on a previous intradermal influenza vaccination studies on elderly patients with chronic illness (12). The seroconversion rate of the IQ group was assumed to be superior to the control IM group, and the seroconversion rate for the A(H1N1) strain by the intradermal and intramuscular seasonal influenza vaccination to be 35% and 20% respectively. With a power of 80% and a two-sided type 1 error of 5%, 40 participants would be needed for each treatment arm that would also allow for a 5% loss to follow-up rate. ANOVA was used to compare the demographic parameters and the immunogenicity among the four different groups. IBM SPSS Statistics 20.0™ was used for statistical computation. A P value<0.05 was considered to represent significant difference.

Results

A total of 160 subjects were enrolled in and completed the study. Forty subjects were randomized equally among the 4 groups. All recruited subjects were healthy volunteers without any past medical history and were not on any regular medications. None of the recruited subjects received influenza vaccination in the previous 5 years. The median age was 20 years (interquartile range 19-21 years) and 50% of the recruited subjects were male. There were no difference in age (p=0.875) and sex (p=0.5) among the four groups.

Safety

No serious adverse events related to vaccination were reported (see Table 1). Incidence of local or systemic adverse events was infrequent and self-limiting. Although grade 1 redness or swelling was more commonly found in IQ and ID groups, there were no differences among the four groups. None of the subjects had visible vaccine leakage from the injection site.

TABLE 1

| | N (%) IQ (n = 40) | ID (n = 40) | IM (n = 40) | NS (n = 40) | p-Value |
|---|---|---|---|---|---|
| Redness | | | | | |
| Grade 1 | 5 (12.5) | 3 (7.5) | 1 (2.5) | 1 (2.5) | 0.20 |
| Grade 2 | 0 (0) | 0 (0) | 0 (0) | 0 (0) | NA |
| Swelling | | | | | |
| Grade 1 | 7 (17.5) | 5 (12.5) | 3 (7.5) | 2 (5) | 0.28 |
| Grade 2 | 3 (7.5) | 3 (7.5) | 0 (0) | 1 (2.5) | 0.26 |

TABLE 1-continued

| | N (%) IQ (n = 40) | ID (n = 40) | IM (n = 40) | NS (n = 40) | p-Value |
|---|---|---|---|---|---|
| Pain | | | | | |
| Grade 1 | 4 (10) | 1 (2.5) | 2 (5) | 0 (0) | 0.16 |
| Grade 2 | 0 (0) | 0 (0) | 0 (0) | 0 (0) | NA |
| Fever | 1 (2.5) | 1 (2.5) | 0 (0) | 2 (5) | 0.57 |
| Headache | 0 (0) | 0 (0) | 0 (0) | 1 (2.5) | 0.40 |
| Malaise | 2 (5) | 1 (2.5) | 1 (2.5) | 1 (2.5) | 0.90 |
| Runny nose | 2 (5) | 1 (2.5) | 1 (2.5) | 1 (2.5) | 0.90 |
| Cough | 2 (5) | 0 (0) | 0 (0) | 0 (0) | 0.11 |
| Sore throat | 1 (2.5) | 0 (0) | 1 (2.5) | 2 (5) | 0.58 |
| Nausea | 0 (0) | 0 (0) | 1 (2.5) | 0 (0) | 0.40 |
| Severe adverse events | 0 (0) | 0 (0) | 0 (0) | 0 (0) | NA |

IQ: imiquimod ointment + intradermal vaccine;
ID: aqueous cream + intradermal vaccine;
IM: aqueous cream + intramuscular vaccine;
NS: imiquimod ointment + intradermal normal saline vaccine
Fever: body temperature ≥37.5° C. Redness, swelling, induration and ecchymosis were graded based on size: grade 1, <20 mm; grade 2, 20-50 mm
Pain was graded as follows: grade 1, pain on touch; grade 2, pain when arm is moved.
NA: not applicable.

Immunogenicity by HI and NT Assays for the Vaccine Strains

The day 7 and 21 immunogenicity measurement in all 3 parameters (seroprotection, seroconversion and GMT fold increase) for the A/California/H1N1 strain was determined to be significantly higher in the IQ group than for the three control groups (p<0.0001). Surprisingly, 97.5% and 100% achieved seroconversion and seroprotection respectively against the A/California/H1N1 strain on day 7 and 21 in the IQ group; with a GMT 631 [95% confidence interval (C.I.): 441.4-902] and GMT fold increase of 18 [95% C.I.: 9.9-26.2] on day 7 and a GMT 687.9 [95% C.I.: 476-994] and GMT fold increase of 19.8 [95% C.I.: 11.4-28.3] on day 14 (see Table 2). The day 7 and 21 seroconversion rate and GMT fold increase for both the A/Victoria/H3N2 (which has relatively low immunogenicity) and B/Massachusetts strains were also significantly higher in the IQ group than the three controls (p<0.0001). Similar results were found for the NT assay (see Table 4) achieving a significantly higher GMT (p<0.0001) on day 7 and 21 for all 3 vaccines' strains when compared to the 3 controls: A/California/H1N1 strain [248.3 (95% CI: 132-465.6); 322.1 (95% CI: 176.6-568.1)], A/Victoria/H3N2 strain [140.6 (95% CI: 81.8-241); 201.8 (95% CI: 119.7-340.4)] and B/Massachusetts strain [198.6 (95% CI: 133.7-294.4); 285.1 (95% CI: 193.2-420.7)].

TABLE 2

| | | IQ (n = 40) | ID (n = 40) | IM (n = 40) | SIQ (n = 40) | p-Value |
|---|---|---|---|---|---|---|
| A/California/H1N1 | | | | | | |
| GMT values (95% CI) | Day 0 | 66.8 (50.6-88.2) | 69.2 (49.2-97.2) | 62.3 (40.3-96.6) | 68 (46.1-100.3) | 0.979 |
| | Day 7 | 631 (441.4-902) | 252.6 (181-352.6) | 208.9 (141.9-307.6) | 69.2 (47.4-101) | <0.0001 |
| | Day 21 | 687.9 (476-994) | 316.2 (224.4-445.7) | 285.1 (189-430.1) | 70.8 (49-102.3) | <0.0001 |
| CPMP criteria | | | | | | |
| Day 0 | Seroprotection (%) | 87.5 | 82.5 | 70 | 82.5 | 0.379 |
| Day 7 | Seroprotection (%) | 100 | 95 | 90 | 85 | 0.029 |
| | Seroconversion (%) | 97.5 | 62.5 | 45 | 0 | <0.0001 |

TABLE 2-continued

| | | IQ (n = 40) | ID (n = 40) | IM (n = 40) | SIQ (n = 40) | p-Value |
|---|---|---|---|---|---|---|
| | GMT fold increase value (95% CI) | 18 (9.9-26.2) | 6.1 (3.7-8.4) | 6.4 (3.6-9.1) | 1.1 (1-1.1) | <0.0001 |
| Day 21 | Seroprotection (%) | 100 | 97.5 | 92.5 | 87.5 | 0.074 |
| | Seroconversion (%) | 97.5 | 70 | 55 | 0 | <0.0001 |
| | GMT fold increase value (95% CI) | 19.8 (11.4-28.3) | 8.5 (4.6-12.4) | 10.7 (4-17.4) | 1.1 (1-1.2) | <0.0001 |

A/Victoria/H3N2

| | | IQ | ID | IM | SIQ | p-Value |
|---|---|---|---|---|---|---|
| GMT values (95% CI) | Day 0 | 49 (41.4-57.9) | 49 (40.8-58.7) | 53.4 (43.5-65.6) | 52.4 (43.9-62.8) | 0.862 |
| | Day 7 | 145.4 (124.9-169.2) | 72.9 (60.8-87.4) | 82.2 (68.2-99.1) | 52.9 (43.9-62.8) | <0.0001 |
| | Day 21 | 147.9 (124.6-175.6) | 89.6 (73.4-109.4) | 94.4 (78.4-113.7) | 53.4 (44.9-63.4) | <0.0001 |

CPMP criteria

| | | IQ | ID | IM | SIQ | p-Value |
|---|---|---|---|---|---|---|
| Day 0 | Seroprotection (%) | 85 | 85 | 85 | 90 | 0.892 |
| Day 7 | Seroprotection (%) | 100 | 95 | 95 | 90 | 0.243 |
| | Seroconversion (%) | 75 | 10 | 10 | 0 | <0.0001 |
| | GMT fold increase value (95% CI) | 3.4 (2.9-3.9) | 1.8 (1.3-2.2) | 1.7 (1.4-2) | 1 (1-1) | <0.0001 |
| Day 21 | Seroprotection (%) | 100 | 95 | 97.5 | 92.5 | 0.331 |
| | Seroconversion (%) | 77.5 | 17.5 | 17.5 | 0 | <0.0001 |
| | GMT fold increase value (95% CI) | 3.5 (3-3.9) | 2.4 (1.7-3) | 2 (1.6-2.3) | 1 (1-1.1) | <0.001 |

B/Massachusetts (Yamagata lineage)

| | | IQ | ID | IM | SIQ | p-Value |
|---|---|---|---|---|---|---|
| GMT values (95% CI) | Day 0 | 140.4 (113-174.5) | 145.4 (114.9-184) | 142.9 (112.7-181.2) | 164.1 (131.2-205.1) | 0.761 |
| | Day 7 | 971.6 (743.2-1270.3) | 664.5 (519-850.7) | 382.4 (286.9-509.7) | 182 (143-231.6) | <0.0001 |
| | Day 21 | 971.6 (739.8-1276.1) | 789.8 (607.9-1026.1) | 462.4 (345.5-618.9) | 185.1 (145.3-235.9) | <0.0001 |

CPMP criteria

| | | IQ | ID | IM | SIQ | p-Value |
|---|---|---|---|---|---|---|
| Day 0 | Seroprotection (%) | 100 | 100 | 100 | 100 | 1.000 |
| Day 7 | Seroprotection (%) | 100 | 100 | 100 | 100 | 1.000 |
| | Seroconversion (%) | 90 | 67.5 | 42.5 | 2.5 | <0.0001 |
| | GMT fold increase value (95% CI) | 10.8 (6.5-15.1) | 7.2 (5.3-9.1) | 5.2 (2.8-7.6) | 1.4 (0.7-2.2) | <0.0001 |
| Day 21 | Seroprotection (%) | 100 | 100 | 100 | 100 | 1.000 |
| | Seroconversion (%) | 90 | 67.5 | 50 | 2.5 | <0.0001 |

TABLE 2-continued

|  | IQ (n = 40) | ID (n = 40) | IM (n = 40) | SIQ (n = 40) | p-Value |
|---|---|---|---|---|---|
| GMT fold increase value (95% CI) | 10.9 (6.6-15.2) | 9.7 (6.7-12.6) | 6.4 (3.6-9.1) | 1.5 (0.7-2.3) | <0.0001 |

IQ: imiquimod ointment + intradermal vaccine;
ID: aqueous cream + intradermal vaccine;
IM: aqueous cream + intramuscular vaccine;
NS: imiquimod ointment + intradermal normal saline vaccine;
GMT: geometric mean titer;
CPMP: Committee for Proprietary Medicinal Products;
CPMP guideline: at least one of the following criteria must be met for the viral strain in the vaccine:
GMT fold increase >2.5, seroconversion rate >40% and seroprotection rate >70%.
[Significant P-values in bold]

Cross-protection

Surprisingly, effective cross-protection was demonstrated for all four non-vaccine strains by HI (see Table 3) and NT (see Table 5) assays in the IQ group for A/HK/4851970/14 (H3N2 Switzerland lineage), A/HK/408027/09 (seasonal H1N1), A/WSN/33 (H1N1), and B/HK/418078/11 (Victoria lineage). By HI assay, 70% and 97.5% achieved seroconversion and seroprotection respectively against the A/HK/485197/14 (H3N2 Switzerland lineage) on day 7 in the IQ group, with a GMT 86.7 (95% C.I. 70.8-105.9) and a GMT fold increase of 4.8 [95% C.I.: 3.7-5.9] on day 7. Similar results were demonstrated by the NT assay with GMT 40 (95% C.I. 28.6-55.5) and GMT 42 (95% C.I. 30.1-58.3) on day 7 and 21 respectively, with the IQ group as the only group achieving the satisfactory antibody response according to the CPMP guideline. Immunogenicity measurement in all 3 parameters (seroconversion, seroprotection and GMT fold increase) for all 4 non-vaccine strains was significantly higher in the IQ group than the three controls (p<0.0001).

TABLE 3

|  |  | IQ (n = 40) | ID (n = 40) | IM (n = 40) | NS (n = 40) | p-Value |
|---|---|---|---|---|---|---|
| A/HK/4851970/14 (H3N2 Switzerland-like lineage) |  |  |  |  |  |  |
| GMT values (95% CI) | Day 0 | 23.3 (18.2-29.9) | 27.7 (23.3-33) | 22.5 (17.7-28.6) | 21.4 (18.2-25.2) | 0.321 |
|  | Day 7 | 86.7 (70.8-105.9) | 37.2 (31-44.5) | 32.4 (26.6-39.4) | 22.5 (19.4-26.1) | <0.0001 |
|  | Day 21 | 94.4 (76-117.2) | 40.6 (34-48.3) | 35.9 (29.6-43.5) | 23.3 (20.3-26.7) | <0.0001 |
| CPMP criteria |  |  |  |  |  |  |
| Day 0 | Seroprotection (%) | 42.5 | 55 | 40 | 32.5 | 0.235 |
| Day 7 | Seroprotection (%) | 97.5 | 75 | 62.5 | 32.5 | <0.0001 |
|  | Seroconversion (%) | 70 | 7.5 | 7.5 | 0 | <0.0001 |
|  | GMT fold increase value (95% CI) | 4.8 (3.7-5.9) | 1.5 (1.2-1.8) | 1.7 (1.3-2.1) | 1.1 (1-1.2) | <0.0001 |
| Day 21 | Seroprotection (%) | 95 | 82.5 | 67.5 | 32.5 | <0.0001 |
|  | Seroconversion (%) | 70 | 10 | 10 | 0 | <0.0001 |
|  | GMT fold increase value (95% CI) | 5.2 (3.9-6.5) | 1.7 (1.4-1.9) | 1.8 (1.4-2.2) | 1.2 (1-1.4) | <0.0001 |
| A/WSN (seasonal H1N1) |  |  |  |  |  |  |
| GMT values (95% CI) | Day 0 | 26.3 (20.7-33.4) | 26.3 (19.8-35) | 27.2 (20.3-36.6) | 27.2 (21.1-35.1) | 0.995 |
|  | Day 7 | 86.6 (71.8-104.5) | 38.5 (30.9-47.5) | 34.1 (25.2-46.1) | 27.2 (21.1-35.1) | <0.0001 |
|  | Day 21 | 91.2 (77.1-107.8) | 49 (39.1-61.3) | 39.1 (28.9-52.9) | 27.2 (21.1-35.1) | <0.0001 |

TABLE 3-continued

| | | IQ (n = 40) | ID (n = 40) | IM (n = 40) | NS (n = 40) | p-Value |
|---|---|---|---|---|---|---|
| CPMP criteria | | | | | | |
| Day 0 | Seroprotection (%) | 35 | 42.5 | 47.5 | 45 | 0.704 |
| Day 7 | Seroprotection (%) | 100 | 57.5 | 55 | 45 | <0.0001 |
| | Seroconversion (%) | 75 | 10 | 2.5 | 0 | <0.0001 |
| | GMT fold increase value (95% CI) | 5.8 (2.4-9.2) | 1.7 (1.3-2.2) | 1.3 (1.2-1.5) | 1 (1-1) | <0.0001 |
| Day 21 | Seroprotection (%) | 100 | 72.5 | 65 | 45 | <0.0001 |
| | Seroconversion (%) | 72.5 | 15 | 5 | 0 | <0.0001 |
| | GMT fold increase value (95% CI) | 5.8 (2.4-9.2) | 2.1 (1.3-2.9) | 1.5 (1.3-1.7) | 1 (1-1) | <0.0001 |
| A/HK/408027/09 (prepandemic seasonal H1N1) | | | | | | |
| GMT values (95% CI) | Day 0 | 33.5 (25.3-44.4) | 34.1 (25.4-45.7) | 42.7 (31.4-58) | 35.9 (25.8-49.9) | 0.655 |
| | Day 7 | 83.7 (65.7-106.6) | 56.2 (41.5-76.2) | 56.2 (41.6-75.9) | 39.8 (28.9-54.8) | 0.005 |
| | Day 21 | 85.1 (67.4-107.2) | 61.3 (45.1-83.3) | 68 (50.3-92) | 40.5 (29.5-55.7) | 0.004 |
| CPMP criteria | | | | | | |
| Day 0 | Seroprotection (%) | 67.5 | 65 | 72.5 | 57.5 | 0.563 |
| Day 7 | Seroprotection (%) | 97.5 | 80 | 82.5 | 57.5 | <0.0001 |
| | Seroconversion (%) | 62.5 | 15 | 5 | 2.5 | <0.0001 |
| | GMT fold increase value (95% CI) | 3.6 (2-5.1) | 1.9 (1.5-2.4) | 1.4 (1.2-1.7) | 1.1 (1-1.1) | <0.0001 |
| Day 21 | Seroprotection (%) | 100 | 80 | 87.5 | 60 | <0.0001 |
| | Seroconversion (%) | 65 | 17.5 | 15 | 2.5 | <0.0001 |
| | GMT fold increase value (95% CI) | 3.7 (2.1-5.2) | 2.1 (1.6-2.5) | 1.8 (1.5-2.1) | 1.3 (0.9-1.6) | <0.0001 |
| B/HK/418078/11 (Victoria lineage) | | | | | | |
| GMT values (95% CI) | Day 0 | 38.5 (29.2-50.6) | 44.2 (34.8-56) | 36.5 (26.5-50.3) | 41.2 (33.5-50.6) | 0.75 |
| | Day 7 | 99.4 (79.3-124.6) | 59.2 (47.1-74.4) | 49 (35.1-68.3) | 41.9 (34-51.7) | <0.0001 |
| | Day 21 | 101.2 (80.6-126.9) | 68 (53.4-86.7) | 50.7 (36-71.3) | 42.7 (34.5-52.7) | <0.0001 |
| CPMP criteria | | | | | | |
| Day 0 | Seroprotection (%) | 72.5 | 80 | 75 | 75 | 0.889 |
| Day 7 | Seroprotection (%) | 97.5 | 87.5 | 77.5 | 77.5 | <0.0001 |
| | Seroconversion (%) | 62.5 | 7.5 | 10 | 0 | <0.0001 |
| | GMT fold increase value (95% CI) | 3.2 (2.7-3.8) | 1.5 (1.2-1.8) | 1.5 (1.2-1.8) | 1.1 (1-1.1) | <0.0001 |

TABLE 3-continued

|  |  | IQ (n = 40) | ID (n = 40) | IM (n = 40) | NS (n = 40) | p-Value |
|---|---|---|---|---|---|---|
| Day 21 | Seroprotection (%) | 97.5 | 87.5 | 77.5 | 77.5 | 0.034 |
|  | Seroconversion (%) | 62.5 | 10 | 10 | 0 | <0.0001 |
|  | GMT fold increase value (95% CI) | 3.2 (2.7-3.8) | 1.7 (1.4-2) | 1.6 (1.3-1.9) | 1.1 (1-1.2) | <0.0001 |

IQ: imiquimod ointment + intradermal vaccine;
ID: aqueous cream + intradermal vaccine;
IM: aqueous cream + intramuscular vaccine;
NS: imiquimod ointment + intradermal normal saline vaccine
GMT: geometric mean titer;
CPMP: Committee for Proprietary Medicinal Products;
CPMP guideline: at least one of the following criteria must be met for the viral strain in the vaccine:
GMT fold increase >2.5, seroconversion rate >40% and seroprotection rate >70%.
[Significant P-values in bold]

TABLE 4

|  |  | IQ (n = 40) | ID (n = 40) | IM (n = 40) | NS (n = 40) | p-Value |
|---|---|---|---|---|---|---|
| A/California/H1N1 |  |  |  |  |  |  |
| GMT values (95% CI) | Day 0 | 13.9 (10-19.3) | 16.2 (11-23.8) | 19 (12.1-29.8) | 17.4 (11.4-26.5) | 0.722 |
|  | Day 7 | 248.3 (132-465.6) | 86.7 (44.6-168.3) | 64.6 (37-112.7) | 21.4 (13.6-33.7) | <0.0001 |
|  | Day 21 | 322.1 (176.6-568.1) | 135.8 (68.2-269.8) | 99.5 (55.6-177.8) | 25 (15.6-39.9) | <0.0001 |
| A/Victoria/H3N2 |  |  |  |  |  |  |
| GMT values (95% CI) | Day 0 | 21 (13.5-32.7) | 19.6 (13.2-29.2) | 27.2 (17-43.6) | 21.3 (14.4-31.7) | 0.710 |
|  | Day 7 | 140.6 (81.8-241) | 133.4 (78.9-225.4) | 99.3 (64.3-153.4) | 21.4 (14.3-31.9) | <0.0001 |
|  | Day 21 | 201.8 (119.7-340.4) | 188.4 (115.3-307.6) | 150.7 (97.5-232.3) | 30.2 (20-45.7) | <0.0001 |
| B/Massachusetts (Yamagata lineage) |  |  |  |  |  |  |
| GMT values (95% CI) | Day 0 | 16.8 (11.4-24.7) | 17.4 (11.9-25.5) | 27.7 (16.7-46) | 23.7 (16.7-33.7) | 0.235 |
|  | Day 7 | 198.6 (133.7-294.4) | 124.5 (73.6-170.6) | 97.7 (58.7-162.6) | 27.2 (18.7-39.7) | <0.0001 |
|  | Day 21 | 285.1 (193.2-420.7) | 182 (111.7-267.3) | 169.8 (100.5-287.1) | 27.7 (19-40.5) | <0.0001 |

IQ: imiquimod ointment + intradermal vaccine;
ID: aqueous cream + intradermal vaccine;
IM: aqueous cream + intramuscular vaccine;
NS: imiquimod ointment + intradermal normal saline vaccine

TABLE 5

|  |  | IQ (n = 40) | ID (n = 40) | IM (n = 40) | NS (n = 40) | p-Value |
|---|---|---|---|---|---|---|
| A/Switzerland/9715293/2013 |  |  |  |  |  |  |
| GMT values (95% CI) | Day 0 | 6.7 (5.8-7.8) | 6.8 (5.8-8) | 6.6 (5.6-7.8) | 7.7 (6.5-9.2) | 0.514 |
|  | Day 7 | 39.8 (28.6-55.5) | 16.2 (11.6-22.6) | 10.7 (8.4-13.6) | 7.7 (6.5-9.2) | <0.0001 |
|  | Day 21 | 42 (30.1-58.3) | 23.7 (16.1-35) | 13.9 (10.7-18) | 7.7 (6.5-9.2) | <0.0001 |
| A/WSN seasonal H1N1 |  |  |  |  |  |  |
| GMT values (95% CI) | Day 0 | 18.3 (13.4-24.9) | 25 (17.3-36) | 17.7 (13.2-23.8) | 21 (15-29.4) | 0.424 |
|  | Day 7 | 65.7 (50.5-85.5) | 41.2 (28.2-60.1) | 24.1 (17.5-33.3) | 22.9 (16.4-31.9) | <0.0001 |
|  | Day 21 | 74.1 (56.4-97.5) | 51.6 (36.9-72.1) | 31.3 (22.4-43.7) | 22.9 (16.3-32.2) | <0.0001 |
| A/pre-2009 seasonal H1N1 |  |  |  |  |  |  |
| GMT values (95% CI) | Day 0 | 12.5 (9.9-15.8) | 13.2 (9.4-18.5) | 17.4 (12.2-24.7) | 14.9 (10.6-20.9) | 0.470 |
|  | Day 7 | 44.9 (29.6-68.1) | 17.4 (11.4-26.5) | 21.4 (14.6-31.3) | 15.4 (11.1-21.3) | <0.0001 |
|  | Day 21 | 44.9 (29.6-68.1) | 18 (11.7-27.5) | 25.4 (17.2-37.5) | 15.4 (11.1-21.3) | 0.001 |
| B/Brisbane (Victoria lineage) |  |  |  |  |  |  |
| GMT values (95% CI) | Day 0 | 10.5 (8.2-13.6) | 12.1 (9-16.2) | 12.9 (8.5-19.1) | 12.7 (8.5-19.1) | 0.810 |
|  | Day 7 | 65.8 (45.2-85.5) | 21.7 (15.4-30.8) | 17.1 (11.6-25.1) | 13.2 (8.9-19.9) | <0.0001 |

TABLE 5-continued

|  | IQ (n = 40) | ID (n = 40) | IM (n = 40) | NS (n = 40) | p-Value |
|---|---|---|---|---|---|
| Day 21 | 69.2 (47.1-101.6) | 27.2 (19.1-38.8) | 19 (12.8-28.1) | 13 (8.6-19.5) | <0.0001 |

IQ: imiquimod ointment + intradermal vaccine;
ID: aqueous cream + intradermal vaccine;
IM: aqueous cream + intramuscular vaccine;
NS: imiquimod ointment + intradermal normal saline vaccine Overall, topical imiquimod pretreatment before intradermal influenza vaccination significantly expedited and augmented the immunogenicity of the vaccine strains with at least 10 fold increase in antibody against vaccine strains on day 7. The Inventors found that such treatment can augment the effective breadth of otherwise conventionally formulated seasonal influenza vaccination by providing important and significant cross-protection against non-vaccine influenza strains, with at least about a 4-fold increase in antibody titer. This is especially notable for the hitherto non-included antigenically drifted influenza strain that only emerged after the WHO recommendation on the components of the seasonal influenza vaccine for the forthcoming season. Surprisingly, this novel approach can also induced good immunity against an archived prototype A(H1N1) virus isolated 83 years ago, for which considerable genetic drift would be expected. Compositions and methods of the inventive concept can form part of a vaccination strategy that can have important global healthcare implications and should translate into better clinical protection by reducing the seasonal influenza burden of sick leave, outpatient visits, hospitalization and mortality in both young and elderly subjects. The ability of this approach to generate sufficiently high GMT and seroconversion rate within 7 days against a hitherto non-included influenza virus due to antigenic drift, can provide a highly flexible, safe and inexpensive way to induce rapid and sustained immunity against such newly emerged virus in serologically naïve individuals.

HI antibody assay results also demonstrate that the vaccine strain A/Victoria/H3N2 virus appeared less immunogenic than the A(H1N1) and the influenza B vaccine virus. Nevertheless, the GMT by HI assay for the four non-vaccine strains were similar. NT assay was also performed to confirm the finding of cross-protection in the study group. According to the CPMP guideline, the intradermal vaccination with topical imiquimod pretreatment was the only group achieving the satisfactory antibody response (≥40) with the NT assay. None of the control groups were able to achieve the sufficiently high seroprotection GMT. A third control group with topical imiquimod ointment followed by sham intradermal normal saline injection allowed us to exclude the possible immunogenic effect of the imiquimod pretreatment.

Conventional seasonal influenza vaccination relies on the induction of neutralizing antibodies against the globular head of the viral hemagglutinin. The antibody is short-lived and annual revaccination is necessary to maintain the neutralizing antibody level. The inventors speculate, without wishing to be bound by theory, that the breadth of the influenza vaccine against seasonal antigenic drift or pandemic antigenic shift could be achieved by novel vaccine development targeting the highly conserved protein epitopes or by the addition of an adjuvant. Both approaches would induce cross-protective humoral responses.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for improving an immune response to vaccination, comprising:
- applying a formulation that is delivered topically to a vaccination site at or immediately prior to vaccination, the topical formulation comprising a toll-like receptor 7 agonist or a toll-like receptor 9 agonist;
- introducing an influenza vaccine at the vaccination site, the influenza vaccine comprising a vaccinating influenza strain; and
- removing the topical formulation from the vaccination site after a time interval,
- wherein the topical formulation is selected to provide the toll-like receptor 7 agonist or the toll-like receptor 9 agonist in a quantity sufficient to provide effective antibody response against a non-vaccinating influenza strain that is not present in the influenza vaccine.

2. The method of claim 1, wherein the toll-like receptor 7 agonist is imiquimod.

3. The method of claim 1, wherein the vaccinating viral strain comprises a first influenza virus or a first coronavirus and the non-vaccinating viral strain comprises a second influenza virus or a second coronavirus.

4. The method of claim 1, further comprising the step of applying a barrier over the topical formulation applied to the vaccination site following vaccination.

5. The method of claim 1, wherein the time interval is from 1 to 6 hours.

6. The method of claim 1, wherein the formulation is applied within 5 minutes of introducing the vaccine.

7. The method of claim 1, wherein the formulation provides from 2 mg to 20 mg of the toll-like receptor 7 agonist or the toll-like receptor 9 agonist on application.

8. The method of claim 1, wherein the topical formulation comprises part of an application device.

9. The method of claim 1, wherein the formulation comprises a nano-emulsion of the toll-like receptor 7 agonist.

10. The method of claim 1, wherein the formulation comprises the toll-like receptor 7 agonist or the toll-like receptor 9 agonist in a quantity sufficient to provide an improved antibody titer to the vaccinating influenza strain, relative to an antibody titer generated on vaccination without the formulation.

11. The method of claim 1, wherein the influenza vaccine comprises a multivalent influenza vaccine.

* * * * *

UNITED STATES PATENT AND TRADEMARK OFFICE
CERTIFICATE OF CORRECTION

PATENT NO. : 10,588,903 B2
APPLICATION NO. : 15/745411
DATED : March 17, 2020
INVENTOR(S) : Fan Ngai Hung It is certified that error appears in the above-identified patent and that said Letters Patent is hereby corrected as shown below:

In the Claims

At Column 22, Lines 52 and 53 change "wherein the topical formulation comprises" to --wherein the formulation comprises--

Signed and Sealed this
Fifth Day of January, 2021

Andrei Iancu
*Director of the United States Patent and Trademark Office*